(12) United States Patent
Ueno

(10) Patent No.: US 6,458,836 B1
(45) Date of Patent: Oct. 1, 2002

(54) TREATMENT OF OCULAR HYPERTENSION AND GLAUCOMA

(75) Inventor: Ryuji Ueno, Potomac, MD (US)

(73) Assignee: Sucampo, A.G., Zug (CH)

( * ) Notice: Subject to any disclaimer, the term of this patent is extended or adjusted under 35 U.S.C. 154(b) by 0 days.

(21) Appl. No.: 09/900,021

(22) Filed: Jul. 9, 2001

Related U.S. Application Data

(63) Continuation-in-part of application No. 09/817,046, filed on Mar. 27, 2001, now abandoned, which is a continuation-in-part of application No. 09/730,830, filed on Dec. 7, 2000, which is a continuation-in-part of application No. 09/527,573, filed on Mar. 16, 2000, now abandoned.

(51) Int. Cl.$^7$ ........................ A61K 31/215; A61K 31/14
(52) U.S. Cl. ........................ 514/530; 514/573; 514/913
(58) Field of Search ................................ 514/530, 573, 514/913

(56) References Cited

U.S. PATENT DOCUMENTS

| | | |
|---|---|---|
| 5,001,153 A | 3/1991 | Ueno et al. |
| 5,321,128 A | 6/1994 | Stjernschantz et al. |
| 6,011,062 A | 1/2000 | Schneider et al. |
| 6,030,999 A | 2/2000 | Stjernschantz et al. |

FOREIGN PATENT DOCUMENTS

| | | |
|---|---|---|
| EP | 0 308 135 A2 | 3/1989 |
| EP | 0 364 417 A1 | 4/1990 |
| EP | 0 453 127 A2 | 10/1991 |
| EP | 0 667 160 A2 | 8/1995 |
| WO | WO99/51273 | 10/1999 |

OTHER PUBLICATIONS

W.H. Bee, et al. "Computer–Assisted IRIS Color Analysis in a Chronic Toxicity Study on Rescula Eye–Drops in Cynomolgus Monkeys" 3797–B398 ARVO Annual Meeting, Ft. Lauderdale, FL, May 11–16, 1997.

R. Chau, et al. "Evaluation of Iris Color Changes in Cynamolgus Monkeys Following Administration of Unoprostone Isopropyl Ophthalmic Solution (0.12%) (UIOS) For Two Years" 3568–b–426, ARVO Annual Meeting, Ft. Lauderdale, FL May 9–14, 1999.

Computer–Assisted Iris Color Analysis in a 52–Week ocular Chronic Toxicity Study on Resula® Eye–Drops In Cynomolgus Monkeys May 29, 1997.

Tetsuya Yamamoto, M.D., et al. "Iris–Color Change Developed after Topical Isopropyl Unoprostone Treatment" Journal of Glaucoma vol. 6, No. 6 430–432 (1997).

Peter Watson, et al. "A–Six–month, Randomized, Double–masked Study Comparing Latanoprost with Timolol in Open–angle Glaucoma and Ocular Hypertension" 1996; 103:126–137.

Carl B. Camras, et al. The United States Latanoprost Study Group, "Comparison of Latanoprost and Timolol in Patients with Ocular Hypertension and Glaucoma, A Six–month, Masked, Multicenter Trial in the United States" Ophthalmology 1996: 103: 138–147.

Carl B. Camras, et al., The Latanoprost Study Groups. "Latanoprost, a prostaglandin Analog, for Galucoma Therapy. Efficacy and Safety after 1 Year of Treatment in 198 Patients" Ophthalmology 1996: 103: 1916–1924.

Per J. Wistrand, et al. "The Incidence and Time–Course of Latanoprost–Induced Iridial Pigmentation as a Function of Eye Color" Survey of Ophthalmology, 1997 vol. 41, Supplement 2, S129–S138.

Ikuo Azuma, et al. "Double–masked Comparative Study of UF–021 and Timolol Ophthalmic Solutions in Patients with Primary Open–Angle Galucoma or Ocular Hypertension" Japan Journal of Ophthalmol, vol. 37, 514–525, 1993.

Tetsuya Yamamoto, et al. "Clinical Evaluation of UF–021 (Rescula®; isopropyl unoprostene)" Survey of Ophthalmology 1997, vol. 41, Supplement 2 S99–S103.

Johan Stjernschantz, et al. "preclinical Pharmacology of Latanoprost, a Phenyl–substituted $PGF_{2\alpha}$ Analogue" Advances in Prostaglandin, Thromboxane, and Leukotriene Research, vol. 23, pp. 513–518.

Yasumasa Goh, et al., "Pharmacological Characterization of Prostaglandin–related Ocular Hypotensive Agents" Japan Journal of Ophthalmol 1994, vol. 38, 236–245.

Barrer, Michele "Unoprostone therapy may have a dual mode of action" Ophthalmology Times Mar. 15, 1999; vol. 24, No. 6, p. 22 (1).

Selene, Goran, et al. "Prostaglandin–Induced Iridial Pigmentation in Primates" Survey of Ophthalmology, vol. 41, Supplement 2, pp. S125–S128, Feb. 1997.

Abstract, The $6^{th}$ Meeting of Japan Glaucoma Society, vol. 5, Special Issue, 1995, No. 240 (and English translation).

PCT International Search Report.

*Primary Examiner*—Zohreh Fay
(74) *Attorney, Agent, or Firm*—Sughrue Mion, PLLC

(57) ABSTRACT

Disclosed is treatment of ocular hypertension and glaucoma by long-term therapy with a prostaglandin related compound for eliminating or reducing potential iridic pigmentation. Composition useful for the treatment, and use of the prostaglandin related compound for producing the composition are also disclosed.

25 Claims, No Drawings

TREATMENT OF OCULAR HYPERTENSION AND GLAUCOMA

This application is a continuation-in-part application of U.S. Ser. No. 09/817,046 filed Mar. 27, 2001, now abandoned in turn a continuation-in-part application of U.S. Ser. No. 09/730,830 filed Dec. 7, 2000, now abandoned in turn a continuation-in-part application of U.S. Ser. No. 09/527,573 filed Mar. 16, 2000, now abandoned.

DESCRIPTION

BACKGROUND OF THE INVENTION

The present invention relates to the long-term treatment and prophylactic management of intraocular pressure in human patients. Further, the present invention relates to a composition useful for said treatment and management. Further more, the present invention relates to use of a specific compound for manufacturing said pharmaceutical composition. More specifically, the present invention relates to the long term management of hypertension or glaucoma in the eyes of human patients, without causing pigmentation or with causing comparatively minimal pigmentation of the iris, by periodic topical ocular application of a prostaglandin related compound.

Prostaglandins (hereinafter, referred to as PG(s)) are members of a class of organic carboxylic acids, which are contained in tissues or organs of human and most other animals, and exhibit a wide range of physiological activity. PGs found in nature (primary PGs) generally have a prostanoic acid skeleton as shown in the formula (A):

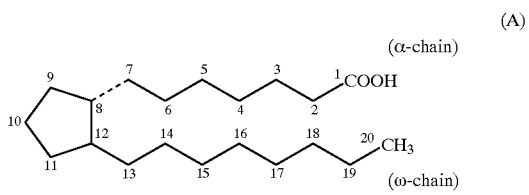

On the other hand, some of the synthetic analogues of primary PGs have a modified skeleton. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH

Subscript 2: 5,6- and 13,14-diunsaturated-15-OH

Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

In addition, some 15-keto (i.e. having an oxo group at position 15 in place of the hydroxy group) prostaglandins and 13,14-dihydro-15-keto-prostaglandins are known as substances naturally produced by enzymatic reactions during in vivo metabolism of primary PGs. 15-keto PGs have been disclosed in, for example, EP-A-0281239, EP-A-0281480, EP-A-0289349, EP-A-0453127 and EP-A-0690049. These cited references are herein incorporated by reference.

At present, Latanoprost is available commercially in the United States for use as a topical ocular hypotensive and an anti-glaucoma agent. Chemically, Latanoprost is a 13,14-dihydro-17-phenyl-18,19,20-trinor $PGF_{2\alpha}$ isopropyl ester. One side effect of Latanoprost is a brown pigmentation of the iris found in about 10% or more of the human patients treated with Latanoprost for about three or more months for management of elevated intraocular pressure. Latanoprost possesses a substantial specific binding affinity for the FP receptor. Selen et al have reported that $PGF_2\alpha$-IE, $PGE_2$-IE and latanoprost induced increased iridial pigmentation in cynomolgus monkeys (Survey of Ophthalmology, 41, supplement 2, S125-S128 (1997)). ("IE" means isopropyl ester.)

Unoprostone isopropyl ophthalmic solution (Rescula®) has been commercially available outside Europe and the United States for topical application in the treatment of ocular hypertension and glaucoma. Unoprostone isopropyl is a docosanoid, namely 13,14-dihydro-15-keto-20-ethyl $PGF_{2\alpha}$ isopropyl ester. To the inventor's best knowledge, Resucla® has not been commercially used by Caucasians in the management of ocular hypertension or glaucoma by its periodic topical application to the eye at least once a day for a period of at least six months, more than one year prior to the filing date of this application. Preliminary results regarding no iridic pigmentation from a long-term monkey trial with Unoprostone isopropyl have been published. Resucla® exhibits substantial absence of FP receptor stimulatory activity.

15-keto-latanoprost (13,14-dihydro-15-keto-17-phenyl-18, 19, 20-trinor $PGF_{2\alpha}$ isopropyl ester) is a promising candidate for use as a topical ocular hypotensive drug. Short-term studies of its use have been reported in U.S. Pat. No. 5,321,128.

SUMMARY OF THE INVENTION

The present invention provides methods for the long-term treatment and prophylactic management of ocular hypertension and glaucoma in human patients without causing pigmentation or with causing less pigmentation than latanoprost of the patient's iris, by periodic topical administration of a prostaglandin related compound.

The present invention also provides a composition suitable for the long-term treatment and prophylactic management of ocular hypertension and glaucoma in human patients by periodic topical ocular administration, which comprises a prostaglandin related compound as an active ingredient.

The present invention also provides use of a prostaglandin related compound for producing a pharmaceutical composition suitable for the long-term treatment and prophylactic management of ocular hypertension and glaucoma in human patients by periodic topical ocular administration.

According to the present invention, the term "prostaglandin related compound" (hereinafter, referred as "PG related compound") includes any of derivatives or analogs (including substituted derivatives) of a compound having the prostanoic acid basic structure irrespective of the configuration of the 5-membered ring, number of double bonds in the α or ω-chain, presence or absence of hydroxy and oxo groups or any other substituent, or any other modification.

The nomenclature of the PG related compounds used herein is based on the numbering system of the prostanoic acid skeleton represented in the above formula (A).

The formula (A) shows a basic skeleton of 20 carbon atoms, but the PG related compounds in the present invention are not limited to those having a 20 carbon atom skeleton. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents PG compounds having hydroxy group (s) at positions 9 and/or 11, but in the present specification, these terms also include those PG related compounds having substituents other than the hydroxy group at positions 9 and/or 11 . Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy compound.

As stated above, the nomenclature of the PG related compounds is based on the prostanoic acid skeleton. However, in case the compound has a similar partial construction as a prostaglandin, the abbreviation of "PG" may be used. Thus, a PG compound of which α-chain is extended by two carbon atoms; that is, having 9 carbon atoms in the α-chain, is named as 2-decarboxy-2- (2-carboxyethyl)-PG compound. Similarly, a PG compound having 11 carbon atoms in the α-chain is named as 2-decarboxy-2-(4-carboxybutyl)-PG compound, and a PG compound having 10 carbon atoms in the ω-chain is named as 20-ethyl-PG compound. These compounds, however, may also be named according to the IUPAC nomenclatures.

The PG related compounds used in the present invention may include any of PG derivatives or analogs. Accordingly, for example, a $PG_1$ compound having a double bond at 13–14 position and a hydroxy group at 15-position, a $PG_2$ compound having another double bond at 5–6 position, a $PG_3$ compound having further double bond at 17–18 position, a 15-keto-PG compound having an oxo group in place of the hydroxy group at the 15-position, a 15-dehydroxy-PG compound having a hydrogen atom in place of the hydroxy group at the 15-position, or the corresponding 13,14-dihydro-PG compounds wherein in each type of compound the double bond at 13–14 position is single bond, or the corresponding 13,14-didehydro-PG compounds wherein in each type of compound the double bond at the 13–14 position is a triple bond are included. Moreover, examples of substituted compounds and derivatives include a compound wherein the terminal carboxyl group in the α-chain of the above described compound is ester, ether, amide, a pharmaceutically acceptable salt thereof, a compound wherein the number of carbon atoms in the α- or ω-chain is decreased or increased, a compound having side chains (e.g., 1 to 3 carbon atoms) on α- or ω-chains, a compound having substituent(s) such as hydroxy, halogen, lower alkyl, hydroxy(lower)alkyl, and oxo, or double bond (s) on the five-membered ring, a compound having substituent(s), such as halogen, oxo, aryl and heterocyclic on the α-chain, a compound having substituents such as halogen, oxo, hydroxy, lower alkoxy, lower alkanoyloxy, cyclo(lower)alkyl, cyclo(lower)alkyloxy, aryl, aryloxy, heterocyclic group and heterocyclic-oxy group on the ω-chain, and a compound having substituent such as lower alkoxy, lower alkanoyloxy, cyclo(lower)alkyl, cyclo(lower) alkyloxy, aryl, aryloxy, heterocyclic group and heterocyclic-oxy group at the terminal of the ω-chain of which is shorter, the same as or longer than that of normal prostanoic acid.

In preferred embodiments, the human patients are of the Caucasian race.

In preferred embodiments, the periodic administration is at least once a day for at least six months.

In another preferred embodiment of the invention, the compound administered is a docosanoid.

In yet another preferred embodiment of the invention, the compound administered is Unoprostone isopropyl.

In still another preferred embodiment of the invention, the compound administered is 15-keto-latanoprost.

In another preferred embodiment of the invention, the compound administered is 17-phenyl-18, 19, 20-trinor $PGF_2\alpha$ N-ethylamide 15-keto-17-phenyl-18,19,20-trinor-$PGF_2\alpha$ N-ethylamide or 13,14-dihydro-15-keto-17-phenyl-18,19,20-trinor $PGF_2\alpha$ N-ethylamide.

In still another preferred embodiment of the invention, the compound administered is a 15-keto-16-(3-trifluoro methyl phenoxy)-17,18,19,20-tetranor $PGF_2\alpha$ or a 13, 14-dihydro-15-keto-16-(3-trifluoromethyl phenoxy)-17,18,19,20-tetranor $PGF_{2\alpha}$, especially their isopropyl esters.

DETAILED DESCRIPTION OF THE INVENTION

The present invention is directed to the long-term care and management of intraocular pressure and glaucoma in human patients. Latanoprost, 13,14-dihydro-17-phenyl-18,19, 20-trinor $PGF_2\alpha$ isopropyl ester, has been used in such treatment, but causes brown pigmentation of the iris of Caucasians in a significant number of patients (10% or more). Since it is not believed at present possible to predict with relative certainty in which patient iridic pigmentation will occur, this is a significant side effect in a color-conscious world, especially for female patients. The iridic pigmentation usually occurs by three or more months with continuous treatment, i.e., periodic administration on a daily basis. It is believed that the iridic pigmentation results from latanoprost's high specific binding affinity for the prostaglandin FP or EP receptor. (*Journal of Japan Glaucoma Society*, 5, 136 (1995))

Now, it has been found that a prostaglandin related compound of the present invention which substantially does not stimulate the prostaglandin FP receptor or possesses an FP specific affinity one-tenth or less than that of latanoprost and is otherwise usable as a topically administered ocular hypotensive, can be safely administered to humans over prolonged time periods without causing dark colored iridic pigmentation. Certain of these compounds are those in which carbon atom number 15 is substituted by an oxo group (15-keto compounds), or those in which carbon atom number 15 is substituted by a hydroxy group and the omega chain beyond carbon atom number 15 contains a straight chain of at least 6 carbon atoms or a straight chain of at least 3 carbon atoms with a ring at the terminal of the omega chain. As above discussed, the compounds of this invention can safely be administered topically for ocular hypotensive effect to human patients over prolonged time periods without causing the brown iridic pigmentation found with Latanoprost.

Prostaglandin related compounds of the present invention and of the following formula (I) are one preferred embodiment.

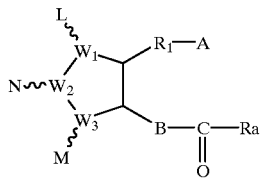
(I)

wherein $W_1$, $W_2$ and $W_3$ are carbon or oxygen atoms,

L, M and N are hydrogen atom, hydroxy, halogen atom, lower alkyl, lower alkoxy, hydroxy(lower)alkyl, or oxo, wherein at least one of L and M is a group other than hydrogen, and the five-membered ring may have at least one double bond;

A is —$CH_2OH$, —$COCH_2OH$, —COOH or a functional derivative thereof;

B is single bond, —$CH_2$—, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$—, or —$CH_2$— C≡C—;

$R_1$ is a saturated or unsaturated bivalent lower or medium aliphatic hydrocarbon residue, which is unsubstituted or substituted with halogen, an alkyl group, hydroxy, oxo, aryl or heterocyclic group; and Ra is a saturated or unsaturated lower or medium aliphatic hydrocarbon residue, which is unsubstituted or substituted with halogen atom, oxo, hydroxy, lower alkyl, lower alkoxy, lower alkanoyloxy, cyclo(lower)alkyl, cyclo(lower)alkyloxy, aryl, aryloxy, heterocyclic group or heterocyclic-oxy group; cyclo(lower)alkyl; cyclo(lower)alkyloxy; aryl; aryloxy; heterocyclic group; heterocyclic-oxy group.

A group of particularly preferable compounds among the above described compounds is represented by the general formula (II):

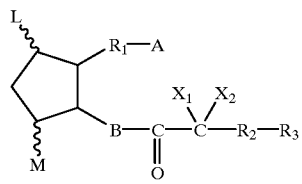
(II)

wherein L, M, $R_1$, A and B are the same definitions described above.

$X_1$ and $X_2$ are hydrogen, lower alkyl, or halogen;

$R_2$ is a single bond or lower alkylene; and $R_3$ is lower alkyl, lower alkoxy, cyclo(lower)alkyl, cyclo(lower)alkyloxy, aryl, aryloxy, heterocyclic group or heterocyclic-oxy group.

Another preferred embodiment of this invention resides in prostaglandin related compounds of the present invention and of the formula (III):

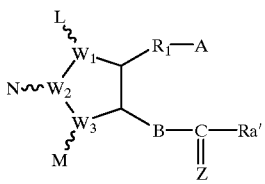
(III)

wherein $W_1$, $W_2$ and $W_3$ are carbon or oxygen atoms,

L, M and N are hydrogen atom, hydroxy, halogen atom, lower alkyl, lower alkoxy, hydroxy(lower)alkyl, or oxo, wherein at least one of L and M is a group other than hydrogen, and the five-membered ring may have at least one double bond;

A is —$CH_2OH$, —$COCH_2OH$, —COOH or a functional derivative thereof;

B is single bond, —$CH_2$—, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$—, or —$CH_2$— C≡C—;

$R_1$ is a saturated or unsaturated bivalent lower or medium aliphatic hydrocarbon residue, which is unsubstituted or substituted with halogen, an alkyl group, hydroxy, oxo, aryl or heterocyclic group;

Z is

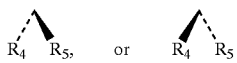

wherein $R_4$ and $R_5$ are hydrogen atom, hydroxy, halogen atom, lower alkyl, lower alkoxy or hydroxy(lower)alkyl, wherein $R_4$ and $R_5$ are not hydroxy, lower alkoxy and/or hydroxy (lower) alkyl at the same time; and Ra' comprises (1) a saturated or unsaturated $C_3$ to $C_5$ straight chain aliphatic hydrocarbon beyond carbon atom number 15 substituted by cyclo (lower) alkyl, cyclo (lower) alkyloxy, aryl, aryloxy, heterocyclic group or heterocyclic oxy group at its terminus or (2) a saturated or unsaturated at least $C_6$ straight chain aliphatic hydrocarbon residue beyond carbon atom number 15, which is unsubstituted or substituted with halogen atom, oxo, hydroxy, lower alkyl, lower alkoxy, lower alkanoyloxy, cyclo(lower)alkyl, cyclo(lower)alkyloxy, aryl, aryloxy, heterocyclic group or heterocyclic-oxy group.

Still another preferred embodiment of this invention resides in prostaglandin related compounds of the present invention and of the formula (IV):

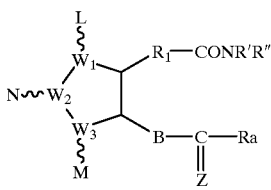
(IV)

wherein $W_1$, $W_2$, and $W_3$ are carbon or oxygen atoms,

L, M and N are hydrogen atom, hydroxy, halogen atom, lower alkyl, lower alkoxy, hydroxy(lower)alkyl, or oxo, wherein at least one of L and M is a group other than hydrogen, and the five-membered ring may have at least one double bond;

R' and R" is hydrogen atom, lower alkyl, aryl, alkyl- or aryl-sulfonyl, lower alkenyl and lower alkynyl;

B is single bond, —CH$_2$—, —CH$_2$—CH$_2$—, —CH=CH—, —C=C—, CH$_2$—CH$_2$—CH$_2$—, —CH=CH—CH$_2$—, —CH$_2$CH=CH—, —C≡C—CH$_2$—, or CH$_2$—C≡C—;

R$_1$ is a saturated or unsaturated bivalent lower or medium aliphatic hydrocarbon residue, which is unsubstituted or substituted with halogen, an alkyl group, hydroxy, oxo, aryl or heterocyclic group;

Z is

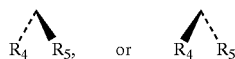

wherein R$_4$ and R$_5$ are hydrogen atom, hydroxy, halogen atom, lower alkyl, lower alkoxy or hydroxy(lower)alkyl, wherein R$_4$ and R$_5$ are not hydroxy, lower alkoxy and/or hydroxy(lower)alkyl at the same time; and Ra is a saturated or unsaturated lower or medium aliphatic hydrocarbon residue, which is unsubstituted or substituted with halogen atom, oxo, hydroxy, lower alkyl, lower alkoxy, lower alkanoyloxy, cyclo(lower)alkyl, cyclo(lower))alkyloxy, aryl, aryloxy, heterocyclic group or heterocyclic-oxy group; cyclo(lower)alkyl; cyclo(lower)alkyloxy; aryl; aryloxy; heterocyclic group; heterocyclic-oxy group.

The compounds used with the present invention can be of the prostaglandins A, B, C, D, E, F, or J type and include subtypes 1, 2, and 3, all as explained in U.S. Pat. No. 5,001,153, the entire content of which is incorporated herein by reference. Compounds usable in the present invention are described in U.S. Pat. No. 5,001,153, and in U.S. Pat. No. 5,312,128, including their ophthalmic preparations.

In the above formula, the term "unsaturated" in the definitions for R$_1$, Ra and Ra' is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms for R$_1$ and 1 to 10, especially 1 to 8 carbon atoms for Ra.

The term "halogen atom" covers fluorine, chlorine, bromine and iodine. Particularly preferable is a fluorine atom.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkoxy" refers to a group of lower alkyl—O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl—O—, wherein cyclo(lower)alkyl is as defined above.

The term "aryl" may include unsubstituted or substituted aromatic hydrocarbon rings (preferably monocyclic groups), for example, phenyl, naphthyl, tolyl, and xylyl. Examples of the substituents are halogen atom, lower alkoxy and halo (lower)alkyl, wherein halogen atom and lower alkyl are as defined above.

The term "aryloxy" refers to a group represented by the formula ArO—, wherein Ar is aryl as defined above.

The term "heterocyclic group" may include mono- to tri-cyclic, preferably monocyclic heterocyclic group which has a 5 to 14, preferably 5 to 10 membered ring having optionally substituted carbon atom(s) and 1 to 4, preferably 1 to 3, of 1 or 2 types of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazyl, 2-pyrrolinyl, pyrrolidinyl, 2-imidazolinyl, imidazolidinyl, 2-pyrazolinyl, pyrazolidinyl, piperazinyl, morpholino, indolyl, benzothienyl, quinolyl, isoquinolyl, puryl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative," of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino) ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tosyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amides of A mean a group represented by the formula —CONR'R", wherein each of R' and R" is hydrogen atom, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L and M include hydroxy and oxo, and especially, M and L are hydroxy to provide a 5-membered ring structure of, so called, PGF type.

Preferred A is —COOH, —CH$_2$OH, or its pharmaceutically acceptable salt, ester, ether or amide thereof.

Preferred example of $X_1$ and $X_2$ is that at least one of them is halogen, more preferably, both of them are halogen, especially fluorine, that provides a structure of, so called 16,16-difluoro type.

Preferred $R_1$ is an unsubstituted saturated or unsaturated bivalent lower-medium aliphatic hydrocarbon residue. It may preferably have 1–10 carbon atoms, more preferably, 2–8 carbon atoms.

Examples of $R_1$ include, for example, the following groups:

—CH$_2$—CH$_2$—,
—CH$_2$—CH$_2$—CH$_2$—CH$_2$—,
—CH$_2$—CH=CH—CH$_2$—,
—CH$_2$—C≡C—CH$_2$—,
—CH$_2$—CH$_2$—CH$_2$—CH$_2$—CH$_2$—,
—CH$_2$—CH=CH—CH$_2$—CH$_2$—,
—CH$_2$—C≡C—CH$_2$—CH$_2$—,
—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$ —CH$_2$ —CH (CH$_3$) —CH$_2$—
—CH$_2$—CH$_2$—CH$_2$—CH$_2$—CH$_2$—CH$_2$—CH$_2$—CH$_2$—,
—CH$_2$—CH≡CH —CH$_2$ —CH$_2$ —CH$_2$ —CH$_2$ —CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH$_2$—CH$_2$(CH$_3$)— CH$_2$—,

Preferred $R_2$ is a single bond or a saturated or unsaturated bivalent lower to medium aliphatic hydrocarbon residue, which may preferably have 1–10 carbon atoms, more preferably 1–8 carbon atoms, especially 1–6 alkylene.

Preferred $R_3$ is a hydrogen atom, aryl or aryloxy.

Preferred Ra is a hydrocarbon containing 1–10 carbon atoms, more preferably, 1–8 carbon atoms and, especially, that having 7 carbon atoms beyond carbon atom number 15.

Preferred Ra' is a straight chain beyond carbon atom number 15 of at least 6 carbon atoms, or at least 3 carbon atoms with a ring, more preferably a phenyl ring, at the terminal of the omega chain.

Preferred R' and R" is hydrogen atom or C1–6 alkyl, C2–6 alkenyl and C3–6 alkynyl.

The configuration of the ring and the α- and/or ω chains in the present invention may be the same as or different from that of the primary PGs. However, the present invention also includes a mixture of a compound having a primary type configuration and a compound of a non-primary type configuration.

When a 15-keto-PG compound of the present invention has for example a single bond between carbon atom number 13 and 14, the compound may be in the keto-hemiacetal equilibrium by formation of a hemiacetal between hydroxy at position 11 and oxo at position 15.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the compounds used in the invention include both isomers. Further, while the compounds used in the invention may be represented by a structure formula or name based on keto-type regardless of the presence or absence of the isomers, it is to be noted that such structure or name does not intend to exclude the hemiacetal type compound.

The present invention includes any of the isomers such as the individual tautomeric isomers, a mixture thereof, or the optical isomers, a mixture thereof, a racemic mixture, and other steric isomers useful for the same purpose.

Compounds useful in the practice of this invention are 13,14-dihydro-15-keto-20-ethyl PGF$_2$α isopropyl ester; 13,14-dihydro-15-keto-17-phenyl-18,19,20-trinor-PGF$_2$α isopropyl ester; 17-phenyl-18,19,20-trinor-PGF$_2$αN-ethylamide; 15-keto-17-phenyl-18,19,20-trinor PGF$_2$α N-ethylamide; 13,14-dihydro-15-keto-17-phenyl-18,19,20-trinor PGF$_2$α N-ethylamide; 15-keto-16-(3-trifluoromethyl phenoxy)-17,18,19,20-tetranor PGF$_2$α isopropyl ester and 13,14-dihydro-15-keto-(3-trifluoromethyl phenoxy)-17,18,19,20-tetranor PGF$_2$α isopropyl ester.

In the method of the present invention, the above-described compounds are topically administered to the affected eye once or twice a day for at least six months, up to a time period as long as required, to complete treatment for elevated ocular pressure or glaucoma, as needed, or to maintain a prophylactic level for six months or longer, without causing iridic pigmentation, especially the brown pigmentation caused by long term use of Latanoprost.

The pharmaceutical composition of the present invention include ophthalmic solution and ointment. The ophthalmic solution may be prepared by dissolving the active ingredient into sterilized aqueous solution such as saline or buffer. A powder composition for ophthalmic solution to be dissolved before use may also be used. The ophthalmic ointment may be prepared by mixing the active ingredient with ointment base.

The pharmaceutical composition of the present invention will usually have a concentration of less than approximately 0.20% (w/v) of active compound. Preferred concentrations are usually within the concentration range of about 0.00005 to 0.18% (w/v).

The composition of the present invention may further be admixed with any of pharmaceutically active agents in so far as said agent is compatible with the purpose of the present invention.

EXAMPLE 1

813 human subjects, mostly Caucasian, were studied for about one year. One drop of 0.15% Rescula® was administered to each treated eye twice a day. After about the first six months of the trial, there was no reported increase in brown pigmentation of the iris.

EXAMPLE 2

IN VITRO FUNCTIONAL RECEPTOR STUDIES

FP-receptor activity

Functional FP-receptor studies were performed using iris sphincter muscles from cat eyes. The eyes were either used directly after enucleation or stored in ice cold saline overnight. The iris sphincter muscles were prepared, cut in halfs, and mounted in thermostated (37° C.) tissue baths with oxygenated modified Kreb's solution containing indomethacin ($2.8 \times 10^{-6}$ M), atropine ($10^{-7}$ M) and propranolol ($10^{-7}$ M). A resting tension of 150 mg was applied, and the contractile force was measured isometrically after cumulative dosing of test compounds. A manual or automated tissue bath system (Buxco, STC 400) was used for the experiments. For each tissue sample the maximal response was normalized to 100%. The mean response of two to four different preparations was calculated.

$EP_1$-receptor activity

Iris sphincter muscles from bovine eyes were used for studies of $EP_1$-receptor responses. Freshly enucleated bovine eyes were transported on ice from a slaughterhouse. The experiments were performed essentially in the same way as with cat iris sphincters, but since bovine iris sphincter expresses both $EP_1$ and TP-receptors, a TP-receptor agonist (GR32 191B) was added to the tissue baths in concentration of 0.1 $\mu$M.

$EP_2$-receptor activity

Segments of guinea-pig ileum were used to study the effect on $EP_2$-receptors. Male guinea pigs were killed with a blow to the head and bled from the carotid arteries. Circular rings (2–3 mm wide) were taken from the ileum about 10 cm from the caecum, a resting tension of 1 g was applied and the preparation was stimulated by using a Gras S88 stimulator delivering trains of square pulses (frequency 7.5 Hz, pulse duration 0.1 msec, train duration 4 sec) to two parallel platinum electrodes in the bath. The voltage over the electrodes was approximately 20 V, and the interval between trains was 100 seconds. The peak contractile force at each stimulation train was measured. Test compounds were added cumulatively, and the inhibitory effect on the muscle twitch was evaluated. A response was taken when three successive peaks had a similar height.

$EP_3$-receptor activity

Guinea-pig vas deferens was used to assess the effect on $EP_3$-receptors. Tissue segments of about 10 mm were mounted in tissue baths and the experiments were performed essentially in the same way as described for the guinea-pig circular ileum.

Platelet studies of TP and IP/DP receptor activity

The activity of test compounds on platelet aggregation was performed on samples from guinea-pig blood. Blood was collected in Venoject tubes containing sodium citrate (to give a concentration of 10 mM) and centrifuged at 200 G for 10 minutes to obtain platelet rich plasma (PRP). The PRP was removed and the remainder was further centrifuged 2000 G for 15 minutes and the supernatant was used as platelet poor plasma (PPP). Platelet aggregation was measured in a Chrono-Log aggregometer using PPP as a blank. 500 $\mu$l PRP was incubated for 2 minutes at 37° C. and 5 $\mu$l of the test solution was added. The maximal change in light transmission was recorded.

Aggregation of guinea-pig thrombocytes was used to measure the effect on TP receptors. The maximal change in light transmission for each test solution was calculated in percent of the maximal aggregation obtained with stable TxA2 analogue U46619 (3 $\mu$M) in the same batch of PRP.

The activity on IP and DP-receptors was determined from the ability of the compounds to inhibit ADP induced aggregation of guinea pig PRP. The test substance (5 $\mu$l) was added to 500 $\mu$l PRP and incubated at 37° C. for two minutes. ADP (final concentration 10 $\mu$M) was added and the maximal change in light transmission induced by ADP in absence and presence of the test drug in the same batch of PRP was measured and expressed in percent.

Concentration-effect curves were fitted to the data using the logistic sigmoid function.

Table I.

Prostaglandin receptor profile of latanoprost acid and 15-keto-latanoprost acid based on $EC_{50}$ values (moles/l) obtained in smooth muscle bath experiments

| PG-analogues | FP | EP1 | EP2 | EP3 |
|---|---|---|---|---|
| Latanoprost Acid | $1.0 \times 10^{-8}$ | $4.9 \times 10$ | $5.3 \times 10^{-4}$ | $2.8 \times 10^{-5}$ |
| 15-keto Latanoprost Acid | $2.6 \times 10^{-7}$ | $2.8 \times 10^{-5}$ | $>10^{-4}$ | $>10^{-4}$ |

The results in Table I indicate that a concentration of latanoprost acid of only $1.0 \times 10^{-8}$ M is needed to stimulate the FP-receptor at 50% efficacy compared to significantly higher concentrations for the other prostaglandin receptors. This means that latanoprost is a selective agonist for the FP receptor and exerts its biological effect primarily through stimulation of this receptor when administered to the eye in clinical doses. A considerably higher concentration of $2.6 \times 10^{-7}$ M was required for 15-keto-Iatanoprost acid for a similar stimulation of the FP-receptor. Accordingly, the receptor profile study of Table I provides evidence that 15-keto-latanoprost acid is at least ten times less potent than latanoprost acid with respect to the activity on the FP receptor, and has virtually no activity on the other prostaglandin receptors ($EP_1$ $EP_2$, and $EP_3$.).

EXAMPLE 3

AFFINITY PROFILE OF UNOPROSTONE FOR PROSTAGLANDIN RECEPTORS

The studies undertaken were to determine whether Unoprostone isopropyl or its metabolite (the acid obtained by hydrolysis of the isopropyl ester) has affinity for any prostaglandin receptor.

Ligand binding assays and signal transduction studies.

In ligand binding studies, the specificity of labeled Unoprostone isopropyl and the metabolite binding to prostaglandin receptor sites in bovine corpus luteal membranes was determined. This tissue expresses most of the PG receptors including an abundance of FP receptors. In signal transduction studies, the mobilization of intracellular calcium using Fluorescence Imaging technique in the primary culture of human ciliary muscle cells and cyclic AMP generation in rabbit iris-ciliary body was measured.

METHODS

1) Ligand binding assay method

This method is well described in the literature. Briefly, 8–16 nM $^3$H-PGF$_2\alpha$ or $^3$H- Unoprostone isopropyl or the metabolite was incubated in the presence or absence of 1,000-fold excess of unlabeled PGF$_{2\alpha}$ or Unoprostone isopropyl or its metabolite with bovine corpus luteal membranes. Free unbound ligands were separated by rapid filtration using a millipore filtration assembly. Membrane bound radioactivity retained by the filter was counted. It is important to define the following terms for appreciation of the binding data:

Total binding is defined as the amount bound in the absence of unlabeled ligand.
Specific binding is defined as the binding displaced by unlabeled ligand.
Non-specific binding is the binding not displaced by unlabeled ligand.

2) Signal transduction methods

Intracellular calcium mobilization

Human ciliary muscle cells at confluency were loaded with Fura 2-AM. Cells in a petri dish were put in a jacketed chamber mounted on the microscope platform. The chamber was maintained at 37° C. by thermostatically controlled water circulating through the chamber jacket. The cells were then exposed to the excitation wavelengths of 334 and 380 nm with an emission wavelength of 510 nm. Cells were perfused with HEPES buffer with or without test compounds. The intracellular calcium was visualized and photographed using Attofluor RatioVision software program and Zeiss fluorescence microscope.

Results

1) Binding Studies

To optimize the specific binding of $^3$H-Unoprostone isopropyl or the metabolite, initially binding was determined as the function of time, membrane and radioligand concentrations in the presence or absence of unlabeled Unoprostone or PGF$_{2\alpha}$. At 5 minutes, total binding was 21.0 fmoles/mg protein, which did not increase with time up to 60 minutes in bovine corpus luteal membranes.

Tables II and III showed that total binding of $^3$H-Unoprostone isopropyl increased with concentrations of the membrane and radioligand but none of the binding was displaced by unlabeled Unoprostone isopropyl or PGF$_{2\alpha}$ suggesting no specific binding.

Table II.

Total Binding of $^3$H-Unoprostone isopropyl in bovine corpus luteal membranes as a function of membrane concentration.

| Protein Conc. | Total binding: fmoles/mg protein |
|---|---|
| 50 µg | 13.0 ± 2.0 (3) |
| 100 µg | 23.0 ± 6.0 (3) |
| 200 µg | 32.0 ± 8.0 (3) |

Unlabeled Unoprostone isopropyl or PGF$_{2\alpha}$ did not displace any of the above binding.

Table III.

Binding of $^3$H-Unoprostone isopropyl and $^3$H-PGF$_{2\alpha}$ in bovine corpus luteal membranes as a function of concentration.

| $^3$H-Unoprostone isopropyl | | | $^3$H-PGF2α | | |
|---|---|---|---|---|---|
| Conc. (nM) | Total Binding fmoles/mg protein | Specific Binding fmoles/mg protein | Conc. (nM) | Total Binding fmoles/mg protein | Specific Binding fmoles/mg protein |
| 8.0 | 19.4 ± 2.0(3) | 0 | 2.0 | 150.0 ± 16.0(3) | 120.0 ± 15.0(3) |
| 16.0 | 25.5 ± 4.0(3) | 0 | 4.0 | 325.0 ± 25.0(3) | 261.0 ± 27.0(3) |
| 32.0 | 40.0 ± 7.0(3) | 0 | 8.0 | 505.0 ± 75.0(3) | 423.0 ± 40.0(3) |

There were no specific binding sites for Unoprostone isopropyl as shown in the Table IV because none of the unlabeled Unoprostone isopropyl concentrations displaced the bound $^3$H-Unoprostone isopropyl. In contrast, $^3$H-PGF$_{2\alpha}$ was bound specifically to its binding sites. Competition studies showed that 17-phenyl trinor PGE$_1$ (EP$_1$), Butaprost (EP$_2$), sulprostone (EP$_3$) , iloprost (IP), U46619 (TP) and BW245C (DP) did not displace $^3$H-Unoprostone isopropyl from the binding sites suggesting that Unoprostone isopropyl does not bind to DP, EP$_1$, EP$_2$, EP$_3$, IP and TP receptor sites. The metabolite has similar binding profiles as Unoprostone isopropyl, i.e. it does not bind to any PG receptor sites.

Table IV.

Competition for $^3$H-Unoprostone isopropyl or PGF$_{2\alpha}$ binding sites by prostaglandin receptor agonists

| Competing Ligand Unoprostone Isopropyl (µM) | Total $^3$H-Unoprostone isopropyl binding fmoles/mg protein | Specific Binding of $^3$H-Unoprostone isopropyl | Competing Ligand PGF$_{2\alpha}$ (µM) | Total $^3$H-PGF$_2\alpha$ binding nmoles/mg Protein | Specific Binding fmoles/mg Protein |
|---|---|---|---|---|---|
| 2.5 | 7.0 | 0 | 0.062 | 0.56 | 0.07 |
| 5.0 | 6.5 | 0 | 0.25 | 0.56 | 0.15 |
| 8.0 | 6.7 | 0 | 0.5 | 0.56 | 0.25 |
| 16.0 | 7.6 | 0 | 8.0 | 0.56 | 0.42 |

2) Second messenger study: Calcium mobilization

Unoprostone isopropyl or the metabolite at concentrations ranging from 10–1000 nM did not mobilize intracellular calcium in human ciliary muscle cells. Fluprostenol, a FP receptor agonist linked to intracellular calcium mobilization pathway, mobilized calcium. The inability of Unoprostone isopropyl or the metabolite to mobilize intracellular calcium suggests that these compounds have no affinity for EP$_1$ or FP or TP receptors. These receptors are linked to phospholipase C pathway, stimulation of which results in the mobilization of intracellular calcium.

Conclusions

The results of the studies demonstrated that Unoprostone isopropyl or the metabolite does not bind to PG receptor sites.

In addition to the above Examples 2 and 3, Goth et al, Japanese Journal Ophthalmol, 36: 236–245 (1994), investigated the agonistic activity and affinity of Unoprostone (the free acid form) and PhXA34 (also in the free acid form). PhXA34 is an epimeric mixture of 15R and 15S compounds thereby including latanoprost and its 15S-epimer. PhXA34 exhibited ½ the agonistic activity of $PGF_{2\alpha}$, to $PGF_{2\alpha}$ receptors, as determined from contraction of cat iris sphincter, while Unoprostone's agonistic activity was only 1/1600 of that of $PGF_{2\alpha}$. Binding inhibition studies showed that PhXA34 strongly inhibited [$^3$H] $PGF_{2\alpha}$ binding using bovine corpus luteum, which has $PGF_{2\alpha}$ receptors while the binding inhibitory activity of Unoprostone was infinitely weaker than that of $PGF_{2\alpha}$ (<<1/280 of $PGF_{2\alpha}$)

The terminology "causing less pigmentation than latanoprost" means over the same treatment time period of at least six months using a clinically approved dosage of once or twice per day, that the compound used in accordance with the present invention causes less irridic pigmentation in comparable irides and/or causes a reduced frequency of pigmentation in a patient population.

The compounds usable in the present invention are at least five times less potent than latanoprost in stimulating the FP receptor as determined by the test of Example 2 herein. Preferably, the usable compounds are at least about ten times less potent than latanoprost regarding stimulation of the FP receptor. Most preferably, the usable compounds also are those exhibiting virtually no stimulation activity on the $EP_1$, $EP_2$, $EP_3$, TP and IP/DP receptors.

Variations of the invention will be apparent to the skilled artisan.

INDUSTRIAL APPLICABILITY

The process, composition and use of the present invention are useful for long-term treatment of ocular hypertension and glaucoma without causing pigmentation or with causing comparatively minimal pigmentation of the iris.

What is claimed:

1. A process for the long term treatment or prophylactic management of ocular hypertension or glaucoma in a human patient by topical ocular administration of a therapeutically effective amount of a prostaglandin related compound at least once a day for at least six months, the improvement to eliminate or reduce potential pigmentation of the iris of a treated eye occurring by said long-term topical ocular application of a prostaglandin related compound, wherein the compound used has the formula (I)

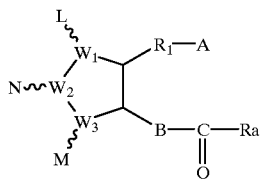

(I)

wherein $W_1$, $W_2$, and $W_3$ are carbon or oxygen atoms,

L, M and N are hydrogen atom, hydroxy, halogen atom, lower alkyl, lower alkoxy, hydroxy (lower)alkyl, or oxo, wherein at least one of L and M is a group other than hydrogen, and the five-membered ring may have at least one double bond;

A is —CH$_2$OH, —COCH$_2$OH, —COOH or a functional derivative thereof;

B is single bond, —CH$_2$—, —CH$_2$—CH$_2$—, —CH=CH—, —C≡C—, —CH$_2$—CH$_2$—CH$_2$, —CH=CH—CH$_2$, —CH$_2$—CH=CH—, —CH≡C—Ch$_2$—, or —CH$_2$—C≡C—;

$R_1$ is a saturated or unsaturated bivalent lower or medium aliphatic hydrocarbon residue, which is unsubstituted or substituted with halogen, an alkyl group, hydroxy, oxo, aryl or heterocyclic group; and Ra is a saturated or unsaturated lower or medium aliphatic hydrocarbon residue, which is unsubstituted or substituted with halogen atom, oxo, hydroxy, lower alkyl, lower alkoxy, lower alkanoyloxy, cyclo(lower)alkyl, cyclo(lower)alkyloxy, aryl, aryloxy, heterodcyclic group or heterocyclic-oxy group; cyclo(lower)alkyl; cyclo(lower)alkyloxy; aryl; aryloxy; heterocyclic group; or hetrocyclic-oxy group.

2. The process of claim 1 wherein the functional derivative of A is salts, ethers, esters or amides.

3. The process of claim 2 wherein the amide of A is represented by the formula —CONR'R", wherein each of R' and R" is hydrogen atom, lower alkyl, aryl, alkyl- or aryl-sulfonyl, lower alkenyl and lower alkynyl.

4. The process of claim 2 wherein the compound used is a 13,14-dihydro-15-keto-20 ethyl $PGF_{2\alpha}$ isopropyl ester.

5. The process of claim 2 wherein the compound used is 15-keto latanoprost.

6. The process of claim 2 wherein the compound used is 15-keto-17-phenyl-18,19,20-trinor $PGF_2\alpha$ N-ethylamide.

7. The process of claim 2 wherein the compound used is 13,14,dihydro-15-keto 17-phenyl-18,1920-trinor $PGF_2\alpha$ N-ethylamide.

8. The process of claim 2 wherein the compound used is 15-keto-16-(3-trifluoromethyl phenoxy)-17,18,19,20-tetranor $PGF_2\alpha$ isopropyl ester.

9. The process of claim 2 wherein the compound used is 13,14-dihydro-15-keto-16-(3-trifluoromethyl phenoxy)-17,18,19,20-tetranor $PGF_2\alpha$ isopropyl ester.

10. The process of claim 1 wherein the compound used is administered twice daily for at least six months.

11. The process of claim 1 wherein the human patient is a Caucasian.

12. the process of claim 1 wherein the compound used contains a 15-keto substituent and an omega chain containing a phenyl ring.

13. A process for the long-term treatment or prophylactic management of ocular hypertension or glaucoma in a human patient by topical ocular administration of a therapeutically effective amount of a prostaglandin related compound at least once a day for at least six months, the improvement to eliminate or reduce potential pigmentation of the iris of a treated eye occurring by said long-term topical ocular application of a prostaglandin related compound, wherein the compound used has the formula (III)

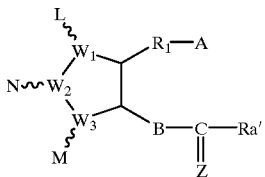

(III)

wherein $W_1$, $W_2$ and $W_3$ are carbon or oxygen atoms,

L, M and N are hydrogen atom, hydroxy, halogen atom, lower alkyl, lower alkoxy, hydroxy(lower)alkyl, or oxo, wherein at least one of L and M is group other than hydrogen, and the five-membered ring may have at least one double bond;

A is —CH₂OH, —COCH₂OH, —COOH or a functional derivative thereof;

B is single bond, —CH₂—, —CH₂—CH₂—, —CH=CH—, —C≡C—, —CH₂—CH₂—CH₂—, —CH=CH—CH₂—, —CH₂—CH=CH—, —C≡C—CH₂—, or —CH₂—C≡C—;

R₁ is a saturated or unsaturated bivalent lower or medium aliphatic hydrocarbon residue, which is unsubstituted or substituted with halogen, an alkyl group, hydroxy, oxo aryl or heterocyclic group;

Z is

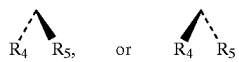

wherein R₄ and R₅ are hydrogen atom, hydroxy, halogen atom, lower alkyl, lower alkoxy or hydroxy(lower) alkyl, wherein R₄ and R₅ are not hydroxy, lower alkoxy and/or hydroxy(lower) alkyl at the same time; and Ra' comprises (1) a saturated or unsaturated C₃ to C₅ straight chain aliphatic hydrocarbon beyond carbon atom number 15 substituted by cyclo (lower) alkyl, cyclo (lower)alkyloxy, aryl, aryloxy, heterocyclic group or heterocyclic-oxy group at its terminus or (2) a saturated or unsaturated at least C₆ straight chain aliphatic hydrocarbon residue beyond carbon atom number 15, which is unsubstituted or substituted with halogen atom, oxo hydroxy, lower alkyl, lower alkoxy, lower alkanoyloxy, cyclo(lower)alkyl, cyclo(lower) alkyloxy, aryl, aryloxy, heterocyclic group or heterocyclic-oxy group.

14. The process of claim 13 wherein the functional derivative of A is salts, ethers, esters or amides.

15. The process of claim 14 wherein the amide of A is represented by the formula —CONR'R", wherein each of R' and R" is hydrogen atom, lower alkyl, aryl, alkyl- or aryl-sulfonyl, lower alkenyl and lower alkynyl.

16. The process of claim 13 wherein the compound used contains a straight chain beyond carbon atom number 15 of at least 6 carbon atoms.

17. The process of claim 16 wherein the compound used is a docosanoid.

18. The process of claim 13 wherein the compound used contains a straight chain beyond carbon atom number 15 of at least 3 carbon atoms substituted by cyclo(lower)alkyl, cyclo(lower) alkyloxy, aryl, aryloxy, heterocyclic group ar heterocyclic-oxy group at the terminus of the omega chain.

19. The process of claim 18 wherein the compound used is substituted by phenyl at the terminus of the omega chain.

20. The process of claim 13 wherein the compound used is administered twice daily for at least six months.

21. The process of claim 13 wherein the human patient is a Caucasin.

22. A process for the long term treatment or prophylactic management of ocular hypertension or glaucoma in a human patient by topical ocular administration in a hyman patient of a therapeutically effective amount of a prostaglandin related compound at least once a day for at least six months, the improvement to eliminate or reduce portential pigmentation of the iris of a treated eye occurring by said long-term topical ocular application of a prostaglandin related compound, wherein the compound used has the formula (IV)

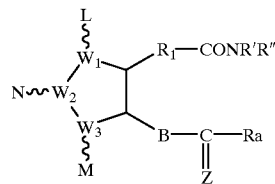

(IV)

wherein W₁, W₂, and W₃ are carbon or oxygen atoms,

L, M and N are hydrogen atom, hydroxy, halogen atom, lower alkyl, lower alkoxy, hydroxy(lower) alkyl, or oxo, wherein at least one of L and M is group other than hydrogen, and the five-membered ring may have at least one double bond;

R' and R" are selected from the group consisting of hydrogen atom, lower alkyl, aryl, aklyl- or aryl-sulfonyl, lower alkenyl and lower alkynyl;

B is single bond, —CH₂—, —CH₂—CH₂—, —CH=CH—, —CH=C—, —CH₂—CH₂—CH₂—, —CH=CH—CH₂—, —CH₂CH=CH—, —C≡C—CH₂—, or —CH₂—C≡C—;

R₁ is a saturated or unsaturated bivalent lower or medium aliphatic hydrocarbon residue, which is unsubstituted or substituted with halogen, an alkyl group, hydroxy, oxo, aryl or heterocyclic group;

Z is

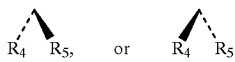

wherein R₄ and R₅ are hydrogen atom, hydroxy, halogen atom, lower alkyl, lower alkoxy or hydroxy(lower) alkyl, wherein R₄ and R₅ are not hydroxy, lower alkoxy and/or hydroxy(lower)alkyl at the same time; and Ra is a saturated or unsaturated lower or medium aliphatic hydrocarbon residue, which is unsubstituted or substituted with halogen atom, oxo, hydroxy, lower alkyl, lower alkoxy, lower alkanoyloxy, cyclo(lower)alkyl, cyclo(lower))alkyloxy, aryl, aryloxy, heterocyclic group or heterocyclic-oxy group; cyclo(lower)alkyl; cyclo(lower)alkyloxy; aryl; aryloxy; heterocyclic group; heterocyclic-oxy group.

23. The process of claim 22 wherein the compound used is 17-phenyl-18,19,20-trinor PGF₂α N-ethylamide.

24. The process of claim 22 wherein the compound used is administered twice daily for at least six months.

25. The process of claim 24 wherein the human patient is a Caucasian.

* * * * *